United States Patent
Fu et al.

(10) Patent No.: US 10,197,553 B2
(45) Date of Patent: Feb. 5, 2019

(54) METHOD FOR ASSESSING THE CONDITION OF A TISSUE SAMPLE WITH POLARIZED ELECTROMAGNETIC RADIATION

(71) Applicant: Hill-Rom Services, Inc., Batesville, IN (US)

(72) Inventors: Yongji Fu, Harrison, OH (US); Eric D. Agdeppa, Cincinnati, OH (US); David L. Ribble, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 358 days.

(21) Appl. No.: 15/091,036

(22) Filed: Apr. 5, 2016

(65) Prior Publication Data

US 2016/0299122 A1    Oct. 13, 2016

Related U.S. Application Data

(60) Provisional application No. 62/153,123, filed on Apr. 27, 2015, provisional application No. 62/144,449, filed on Apr. 8, 2015.

(51) Int. Cl.
*A61B 5/00*    (2006.01)
*G01N 33/483*    (2006.01)
(Continued)

(52) U.S. Cl.
CPC ....... *G01N 33/4833* (2013.01); *A61B 5/0059* (2013.01); *A61B 5/447* (2013.01);
(Continued)

(58) Field of Classification Search
CPC ...... A61B 5/0059; A61B 5/447; G01N 21/21; G01N 2021/4792
See application file for complete search history.

(56) References Cited

U.S. PATENT DOCUMENTS 7,289,211 B1 * 10/2007 Walsh, Jr. ............ A61B 5/0086
356/369
8,463,006 B2    6/2013 Prokoski
(Continued)

FOREIGN PATENT DOCUMENTS

| KR | 20080098248 A | 11/2008 |
|---|---|---|
| WO | 2014121152 A1 | 8/2014 |
| WO | 2014146053 A3 | 9/2014 |

OTHER PUBLICATIONS

Ghassemi et al. "Towards skin polarization characterization using polarimetric technique" J Zheijang Univ Sci B 2009 10 (8): 602-608.*

(Continued)

*Primary Examiner* — Eric D. Bertram
(74) *Attorney, Agent, or Firm* — Kenneth C. Baran

(57) ABSTRACT

A method for assessing the condition of a tissue sample includes the steps of:
1. illuminating the sample with incident electromagnetic radiation exhibiting P polarization types,
2. for each of the P polarization types, inspecting the scattered incident radiation for at least one and possibly all of Q polarization types;
3. establishing a transfer function M relating the intensity of the P polarization types of the incident radiation to the intensity of the polarization types for which the scattered radiation was inspected;
4. comparing the established transfer function to one or more reference transfer functions; and
5. reaching a conclusion about the condition of the tissue sample based on the comparison.

22 Claims, 9 Drawing Sheets

(51) Int. Cl.
*G01N 21/21* (2006.01)
*G01N 21/49* (2006.01)
*G01N 21/47* (2006.01)

(52) U.S. Cl.
CPC .............. *G01N 21/21* (2013.01); *G01N 21/49* (2013.01); *G01N 2021/4792* (2013.01)

(56) References Cited

U.S. PATENT DOCUMENTS

| | | | |
|---|---|---|---|
| 8,792,098 | B2 | 7/2014 | Dewald et al. |
| 8,891,087 | B2 | 11/2014 | Zuzak et al. |
| 2006/0241495 | A1 | 10/2006 | Kurtz |
| 2007/0249913 | A1 | 10/2007 | Freeman et al. |
| 2010/0140461 | A1 | 6/2010 | Sprigle et al. |
| 2015/0327777 | A1 | 11/2015 | Kostic et al. |
| 2017/0102319 | A1* | 4/2017 | De Martino ........... G01N 21/21 |

OTHER PUBLICATIONS

European Search Report Application No. 16164324.2-1666; Reference P/74745.EP01/AF; dated Sep. 13, 2016.

Towards skin polarization characterization using polarimetric technique; Journal of Zheijang University Science B ISSN 1673-1581 (Print); ISSN 1862-1783 (Online).

Detection of Skin Erythema in Darkly Pigmented Skin Using Multispectral Images; Stephen Sprigle, PhD, PT; Liwei Zhang, PhD; and Mark Duckworth, MS; Advances in Skin & Wound Care vol. 22 No. 4; www.woundcarejournal.com; Apr. 2009; 2009 Lippincott Wiliams & Wilkins; whole document.

Imaging skin pathology with polarized light; Steven L. Jacques; Jessica C. Ramella-Roman; Ken Lee; Journal of Biomedical Optics; vol. 7 No. 3; Jul. 2002; whole document.

Imaging Superficial Tissues With Polarized Light; Steven L. Jacques, PhD, Jessica R. Roman, MS, Ken Lee, MD; Lasers in Surgery and Medicine 26:119-129 (2000); 2000 Wiley-Liss, Inc.; whole document.

Polarized Light Scattering Spectroscopy for Quantitative Measurement of Epithelial Cellular Structure in Situ; Vadim Backman, Rajan Gurjar, Kamran Badizadegan, Irving Itzkan, Ramachandra R. Dasari, Lev T. Perelman, and Michael S. Feld; IEEE Journal of Selected Topics in Quantum Electronics, vol. 5, No. 4; Jul./Aug. 1999.

Exogenous Molecular Porbes for Targeted Imaging in Cancer: Focus on Multi-modal Imaging; Bishnu P. Joshi, Thomas D. Wang; Cancers 2010, 2, 1251-1287; doi: 10.3390/cancers2021251; Jun. 11, 1010; www.mdpi.com/journal/cancers.

Two-dimensional depth-resolved Mueller matrix characterization of biological tissue by optical coherence tomography; Gang Yao, Lihong V. Wang; 1999 Optical Society of America; Apr. 15, 1999 / vol. 24, No. 8 / Optics Letters; whole document.

Chapter 19 Polarized light imaging of tissues; Steven L. Jacques, Jessica C. Ramell-Roman; whole document especially sections 19.2.3, 19.3.1, and 19.3.2.

Single sensor that outputs narrowband multispectral images; Linghua Kong, Dingrong Yi, Stephen Sprigle, Fentao Wang, Chao Wang, Fuhan, Liu, Ali Adibi, and Rao Tummala; Journal of Biomedical Optics; Jan./Feb. 2010 Vo. 12(1); JBO Letters.

Non-Invasive Erythema Detection Using Spectral Imaging; Sharon Eve Sonenblum, MS; Stephen Sprigle, Phd, PT; Leanne West, MS; Georgia Institute of Technology; Erythema Detection.

Detecting early stage pressure ulcer on dark skin using multispectral imager; Dingrong Yi, Linghua Kong, and Stephen Springle; Biomedical Vibrational Spectroscopy IV: Advances in Research and Industry; 2010.

Handheld Erythema and Bruise Detector; Linghua Kong, Stephen Sprigle, Mark G. Duckworth, Dingrong Yi, Jayme J. Caspall, Jiwu Wang, and Futing Zhao; Medical Imaging 2008: Computer-Aided Diagnosis, edited by Maryellen L. giger, Nico Karssemeijer, Proc of SPIE vol. 6915, 69153K, (2008).

Principal component model of multispectral data for near real-time skin chromophore mapping; Kainerstorfer; Journal of Biomedical Optics vol. 15(4), 046007Jul. / Aug. 2010.

A non-invasive miniaturized-wireless laser Doppler fiber optic sensor for understanding distal fingertip injuries in astronauts; Ansari, Rafat R. et al; Optical Diagnostics and Sensing IX. Ed. Gerard L. Cote. San Jose, CA, USA: m SPIE. 2009, 718609-9. © 2009 SPIE—The International Society for Optical Engineering.

Polarized Light Examination and Photography of the Skin; R. Rox Anderson MD; archderm.jamanetwork.com/by a Indiana University School of Medicine User on Mar. 3, 2015; 1000 Arch Dermato— vol. 127, Jul. 1991.

* cited by examiner

METHOD FOR ASSESSING THE CONDITION OF A TISSUE SAMPLE WITH POLARIZED ELECTROMAGNETIC RADIATION

CROSS REFERENCE TO RELATED APPLICATIONS

This application claims priority to U.S. provisional applications 62/144,449 filed on Apr. 8, 2015 and 62/153,123 filed on Apr. 27, 2015, both entitled "Method for Assessing the Condition of a Tissue Sample with Polarized Electromagnetic Radiation", the contents of both of which are incorporated herein by reference.

TECHNICAL FIELD

The subject matter described herein relates to the use of polarized electromagnetic radiation for assessing the condition of a tissue sample. One example application is detection of a pressure ulcer or a tissue condition which is a precursor to a pressure ulcer.

BACKGROUND

Nurses, physicians and others involved in the care of patients may need to assess the condition of a patient's tissue for abnormalities. One abnormality of interest is a pressure ulcer. One definition of a pressure ulcer is the International NPUAP-EPUAP Pressure Ulcer Definition which advises "A pressure ulcer is localized injury to the skin and/or underlying tissue usually over a bony prominence, as a result of pressure, or pressure in combination with shear." Pressure ulcers can develop and worsen quickly and can be life threatening. Another abnormality of interest is a deep tissue injury. The National Pressure Ulcer Advisory Panel (NPAUP) defines a deep tissue injury as "A pressure-related injury to subcutaneous tissues under intact skin. Initially, these lesions have the appearance of a deep bruise. These lesions may herald the subsequent development of a Stage III-IV pressure ulcer even with optimal treatment." (NPAUP, 2005). It is therefore desirable to be able to identify deep tissue injuries, pressure ulcers, and tissue conditions which are precursors to pressure ulcers or to at least be able to identify the early stages of these conditions (including at times when the condition may not be readily discernible) so that corrective intervention can be taken before the condition becomes life threatening or difficult to heal.

SUMMARY

A method for assessing the condition of a tissue sample includes the steps of:
1. illuminating the sample with incident electromagnetic radiation exhibiting P polarization types,
2. for each of the P polarization types, inspecting the scattered incident radiation for at least one and possibly all of Q polarization types;
3. establishing a transfer function M relating the intensity of the P polarization types of the incident radiation to the intensity of the polarization types for which the scattered radiation was inspected;
4. comparing the established transfer function to one or more reference transfer functions; and
5. reaching a conclusion about the condition of the tissue sample based on the comparison.

In one example of the method the polarization types of the incident radiation and the polarization types of the scattered radiation are selected from:
 a) linear horizontal polarization designated by H,
 b) linear vertical polarization designated by V,
 c) +45° linear polarization designated by $P^+$,
 d) −45° linear polarization designated by $P^−$,
 e) right circular polarization designated by R, and
 f) left circular polarization designated by L.
and the transfer function M satisfies the matrix cross product:

$$\begin{bmatrix} I \\ Q \\ U \\ V \end{bmatrix}_{OUT} = \begin{bmatrix} M11 & M12 & M13 & M14 \\ M21 & M22 & M23 & M24 \\ M31 & M32 & M33 & M34 \\ M41 & M42 & M43 & M44 \end{bmatrix} \times \begin{bmatrix} I \\ Q \\ U \\ V \end{bmatrix}_{IN}$$

where: I is total light intensity, Q=H−V, U=$P^+$−$P^−$, and V=R−L.

BRIEF DESCRIPTION OF THE DRAWINGS

The foregoing and other features of the various embodiments of the methods and apparatuses described herein will become more apparent from the following detailed description and the accompanying drawings in which.

DETAILED DESCRIPTION

Figure 1:
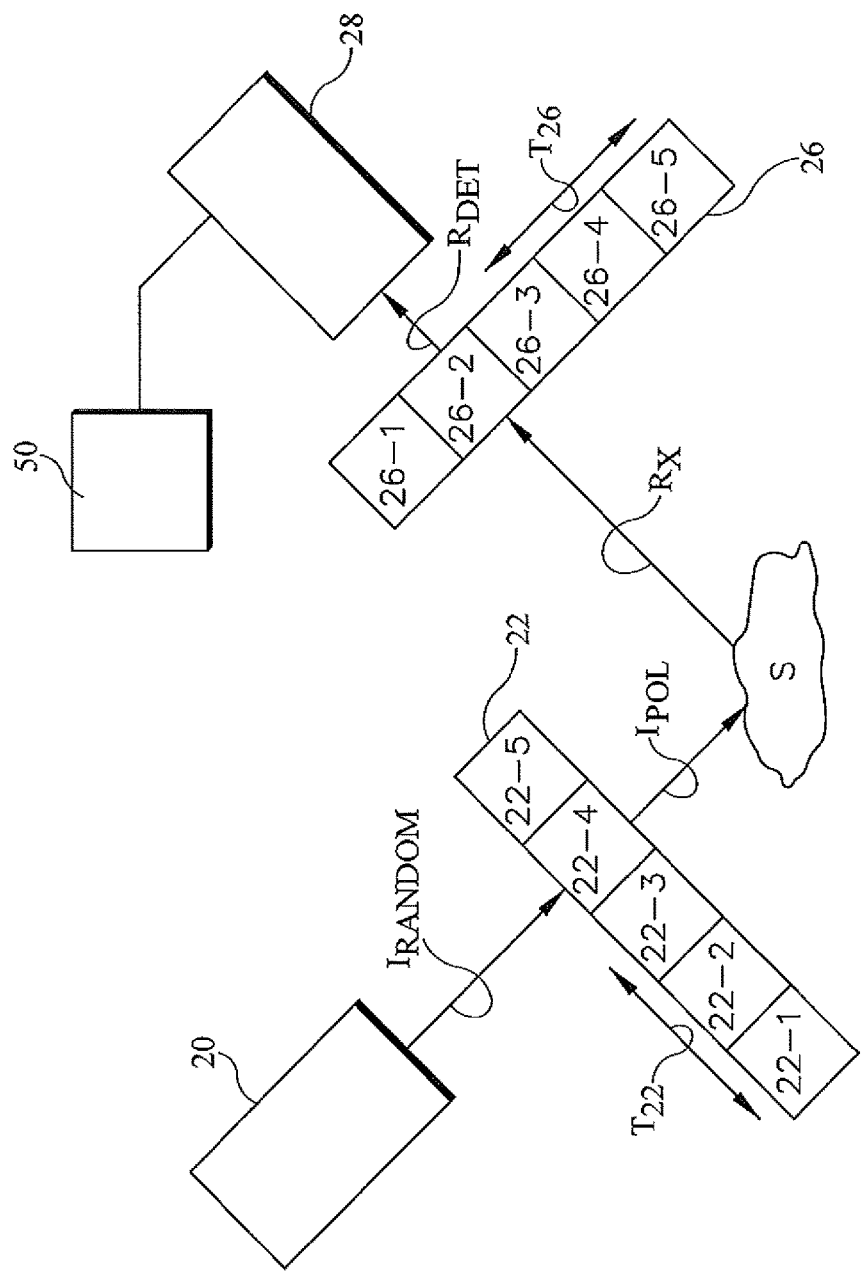
FIG. 1 is a schematic representation of an apparatus which employs polarized electromagnetic radiation to detect the condition of a tissue sample S and which shows an arrangement for sequential illumination of the sample with different types of polarized light.

This specification describes apparatuses and methods which employ polarized electromagnetic radiation to assess the condition of a tissue sample, for example to determine if the sample exhibits an abnormal or unusual condition. One example tissue is skin. Example conditions include pressure ulcers, burns, and scars. In principle, the electromagnetic radiation can correspond to any part of the electromagnetic spectrum however design considerations may commend the use of particular portions of the spectrum. For that reason, and to make the disclosure more concrete, this description will refer to electromagnetic radiation as light, without any intent to limit the generality of the disclosure or claims except when portions of the spectrum (e.g infrared, visible, ultraviolet) are expressly designated. In addition, the word "illuminate" and its variants and synonyms are not restricted to the visible portion of the spectrum but instead describe the act of causing the light (electromagnetic radiation) to be incident upon the tissue sample. In addition, although the examples used in this description are predominantly examples of pressure ulcers, the described apparatuses and methods may be equally applicable to other conditions such as deep tissue injuries and precursors to pressure ulcers.

In this specification features similar to or the same as features previously described may be identified by reference numerals which were previously used.

FIG. 1 schematically illustrates an example apparatus for assessing or evaluating the condition of a tissue sample. The illustrated apparatus includes a light source 20 which produces unpolarized or random light $I_{RAND}$ and an array 22 of polarizers. The illustrated array of polarizers includes five members labeled 22-1 through 22-5. Each polarizer polarizes the random light in a particular way. In other words each polarizer produces a different type of polarized light $I_{POL}$. Examples of various types of polarized light which are useful in the methods described in this specification include the following:
 a) linear horizontal designated by H,
 b) linear vertical designated by V,
 c) +45° linear designated by P$^+$,
 d) −45° linear designated by P$^-$,
 e) right circular designated by R
 f) left circular designated by L.
The designations H, V, P$^+$, P$^-$, R and L are used in this specification to refer to types of polarization as just described and also to refer to the intensity of light which exhibits the designated polarization. In each instance the meaning will be expressly stated or will be clear from context.

The apparatus also includes a polarizing filter array 26. The polarizing filter array includes five members labeled 26-1 through 26-5. Members of the filter array and members of the polarizing array identified by the same suffix (−1, −2, etc.) are associated with the same type of polarization. For example if the "−4" suffix signifies R polarized light, then polarizer 22-4 produces R polarized light, and only R polarized light will pass through filter 26-4. The polarizing array 22 and the filter array 26 are each shown as being translatable in a direction shown by double-headed arrows $T_{22}$ and $T_{26}$ so that a user can select the desired polarizer and filter. The apparatus includes a detector 28. Examples of detectors include a camera or a charge coupled device (CCD). The illustrated apparatus also includes a processor 50 for processing information from the detector.

In the example of FIG. 1 a user has selected polarizer 22-4 and filter 26-2. As a result the input light $I_{POL}$ incident on tissue sample S exhibits the type of polarization associated with polarizer 22-4. The sample affects the polarization so that, in general, the output or scattered light $R_X$ may or may not exhibit the type of polarization imparted by polarizer 22-4 and may exhibit other types of polarization. The methods described in this specification are believed to be most effective if the incident light photons are backscattered from the tissue sample only once or twice rather than being multiply scattered. The user may successively place each of the filters 26-1 through 26-5 in the path of the scattered light to determine which polarization types are present in $R_X$. In the example the only scattered light $R_X$ that will pass through the filter is light whose polarization is the polarization that filter 26-2 is designed to pass. Scattered light that passes through the filter is designated $R_{DET}$ and is collected and detected by detector 28.

Figure 2:
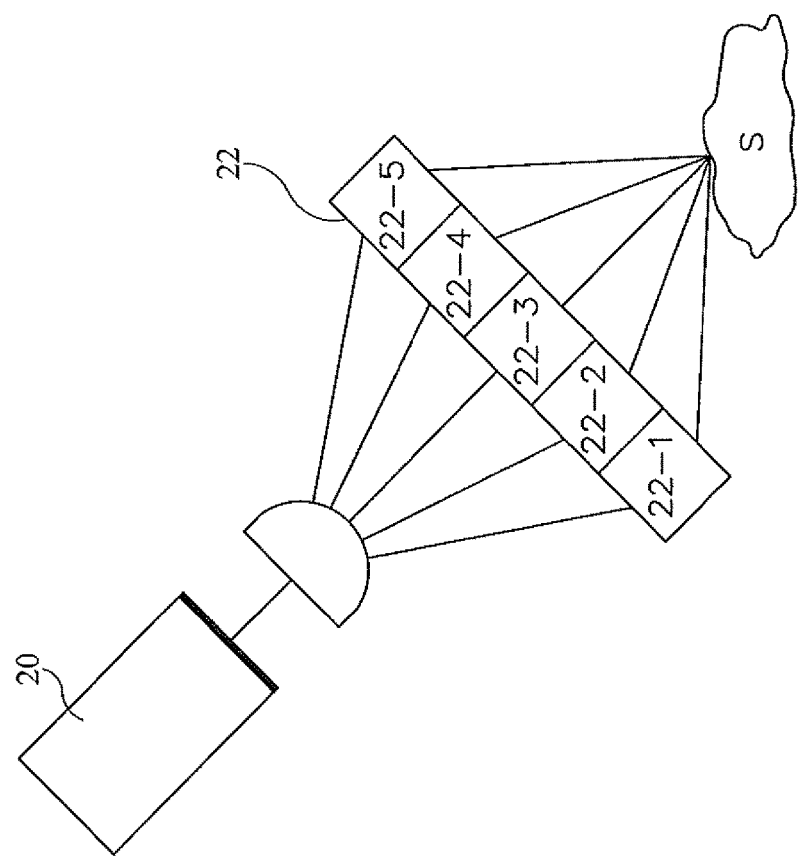
FIG. 2 is a schematic representation of selected components of FIG. 1 showing an arrangement for concurrent illumination of the sample.

FIG. 2 shows an arrangement for applying the illumination of different polarization types concurrently rather than successively. The illumination is carried out concurrently by aiming light of different polarizations on substantially the same point on the tissue or by aiming light of different polarizations on a small region of the tissue. A small region of the tissue is a region small enough that all sites within the region are expected to affect the polarization of polarized incident light in substantially the same way.

As already noted the incident electromagnetic radiation can correspond to any part of the electromagnetic spectrum, however design considerations may motivate the use of radiation from particular portions of the spectrum, for example radiation from the portion of the spectrum which encompasses infrared, visible and ultraviolet wavelengths. If it is necessary to evaluate tissue at some specified depth, for example 0.1 mm beneath the exposed surface of the epidermis, the selected light will be of a wavelength that penetrates the tissue to the prescribed depth and scatters more strongly from the tissue at that prescribed depth and less strongly from less deep tissue. More preferably the selected wavelength is a wavelength to which the less deep tissue is substantially transparent.

Figure 3:
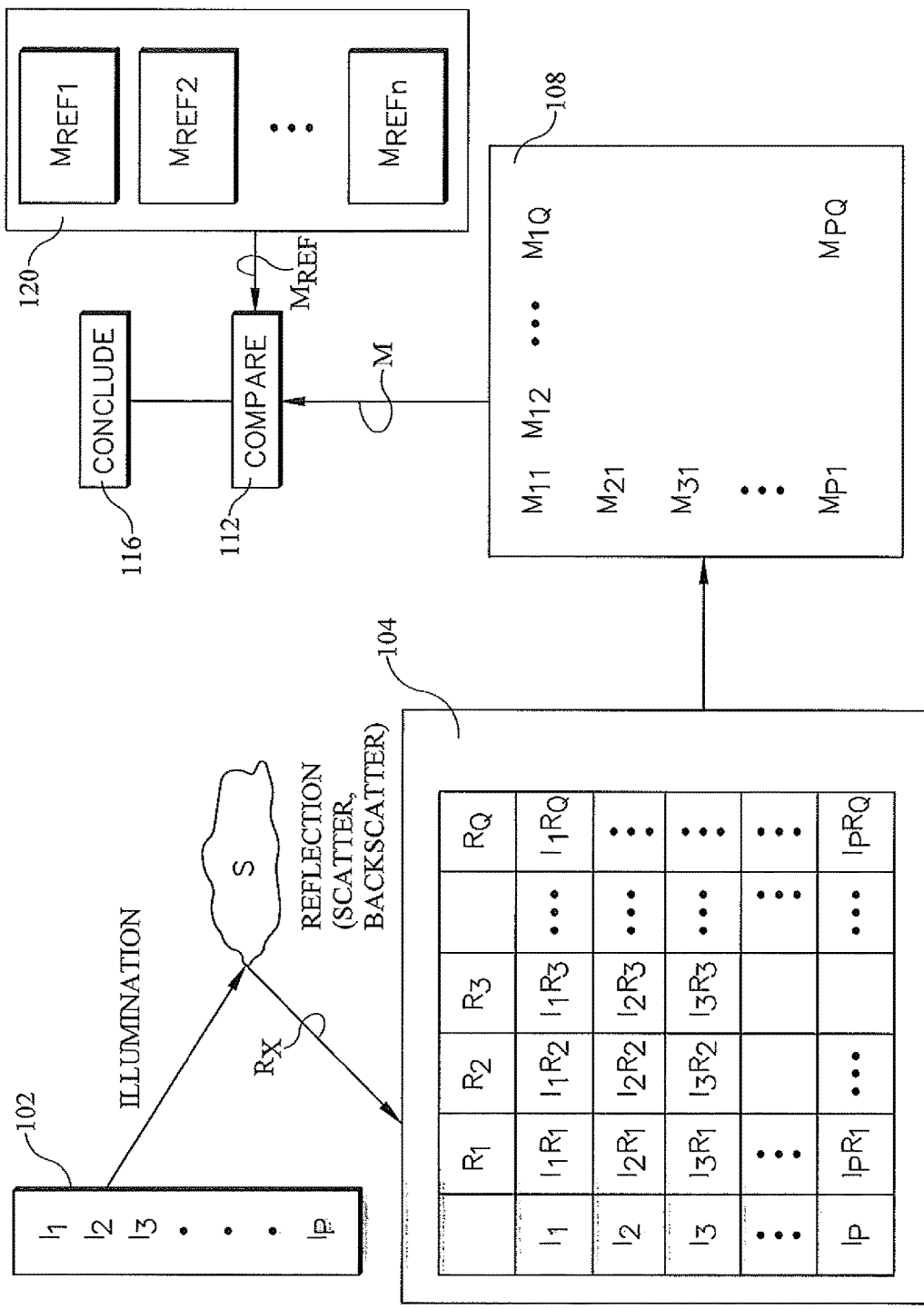
FIG. 3 is a flow chart illustrating a method of assessing the condition of a tissue sample. The method employs library of transfer functions and carries out a comprehensive inspection of light scattered from the tissue sample.

FIG. 3 shows a method for assessing the condition of a tissue sample S. According to the method the sample is successively illuminated with light which exhibits each of P different illumination types (block 102). The light incident on the sample is designated by and the type of polarization is designated by the subscripts 1, 2, . . . P. For each polarization type the incident light is of a known intensity. For each of the P polarization types, $R_X$, the incident light which scattered from the sample, is inspected for the presence and intensity of each of Q polarization types. Block 104 shows this in tabular format using the notation $I_jR_k$ to denote the intensity of k-polarized scattered light $R_x$ resulting from the sample having been illuminated with j-polarized light I of known intensity. For example table entry $I_1R_2$ is the intensity of scattered light having type-2 polarization as a result of the sample having been illuminated with light whose intensity is known and which is type-1 polarized. Similarly table entry $I_3R_3$ is the intensity of scattered light having type-3 polarization as a result of the sample having been illuminated with light whose intensity is known and which is type-3 polarized. Block 104 shows a fully populated table, indicating that the scattering resulting from each of the P types of incident light was inspected for each of the Q types of polarization. Some of the entries may be zero or null entries indicating that the scattering resulting from a type of incident light was not polarized in the way indicated by the subscript of the column heading. The fully populated chart may be referred to as a data matrix.

At block 108 the method establishes a relationship or transfer function M which relates the intensity and polarization type of the incident radiation to the intensity and polarization type of the scattered radiation. In particular block 108 establishes a relationship between the intensity of each of the P polarization types of the incident light and the intensity of the each of the Q polarization types observed in the scattered light. For the fully populated chart of FIG. 3 the transfer function has P×Q elements. Each element of the transfer function has an information content which can be expressed as an intensity $I_j R_k$ or as a sum and/or difference of those intensities. An example of the possible information content of an element is HH+HV+VH+VV where:

1) HH is the intensity of H-polarized scattered light as a result of having illuminated the sample with H-polarized incident light of known intensity,
2) HV is the intensity of V-polarized scattered light as a result of having illuminated the sample with H-polarized incident light of known intensity
3) VH is the intensity of H-polarized scattered light as a result of having illuminated the sample with V-polarized incident light of known intensity and
4) VV is the intensity of V-polarized scattered light as a result of having illuminated the sample with V-polarized incident light of known intensity.

At block 112 the method compares the transfer function M to one or more reference transfer functions. At block 116 the method reaches a conclusion about the condition of the tissue sample based on the comparison. The comparing and concluding steps may be carried out by processor 50 of FIG. 1. Alternatively the comparing and concluding steps may be carried out manually provided the transfer function and the reference transfer functions are in a human-useable form. One possible conclusion is that a pressure ulcer or a condition consistent with a precursor to a pressure ulcer is present in the sample.

As shown in FIG. 3 the one or more reference transfer functions are members of a library 120 of transfer functions $M_{REF1}$, $M_{REF2}$, ... $M_{REFn}$. At least some of the library members, and possibly all of the library members, are designated as conforming to specified tissue conditions, for example a pressure ulcer, a cancer, or a benign irregularity (some library members may conform to only one condition, some may conform to more than one condition). Alternatively, some of the library members might not be known to be representative of a known tissue condition, at least not with enough confidence to justify designating the library transfer function as conforming to a tissue condition. Accordingly, the step of reaching a conclusion about the condition of the tissue sample at block 116 can include:

a) concluding that at least one of the designated library members compares favorably to the sample,
b) concluding that none of the designated library members compares favorably to the sample; and
c) concluding that the condition of the tissue sample is indeterminate.

The concept of a favorable comparison does not require absolute identicality between the reference transfer function and the transfer function of the sample. A comparison which identifies differences no greater than some prescribed tolerance can be accepted as a favorable comparison.

The conclusion that at least one of the designated library members compares favorably to the sample may lead to the further conclusion that the tissue sample exhibits the condition that the library member conforms to (particularly if the library member conforms to only one condition rather than two or more conditions).

The conclusion that none of the designated library members compares favorably to the sample may lead to the further conclusion that the tissue sample exhibits none of the specified conditions that the designated library members conform to.

The conclusion that the condition of the sample is indeterminate can occur for several reasons. One is that too many of the library members conform closely enough to the sample to enable a high confidence conclusion of which library member is the best match. Another is that the sample compares favorably to a library member not known to be representative of a known tissue condition. Another is that the transfer function of the sample compares favorably to a library member that conforms to two or more conditions. In that case, although the condition of the sample will not have been conclusively determined, it will have been narrowed down to the conditions that the library member conforms to.

Figure 4:
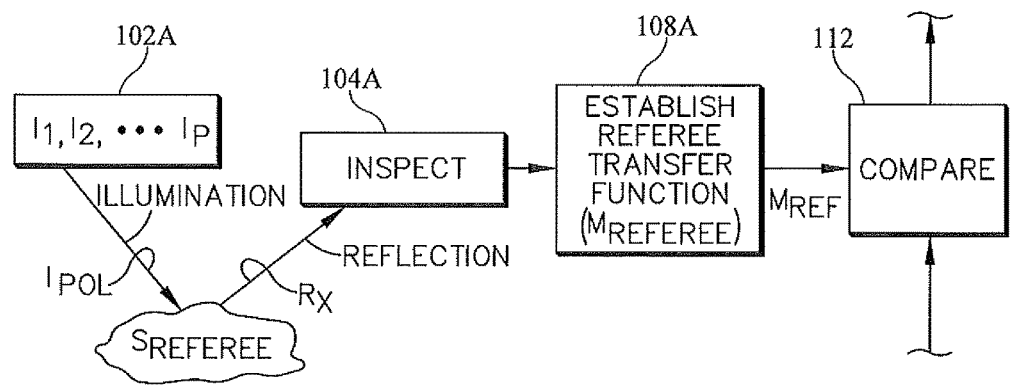
FIG. 4 is a portion of a flow chart illustrating a method, similar to that of FIG. 3, for assessing the condition of a tissue sample but which employs an alternative to the library of FIG. 3.

FIG. 4 shows an option which may be used as an alternative to using an existing library 120 of reference transfer functions. The alternative method includes the step of actively establishing the one or more reference transfer functions $M_{REF}$ rather than using a pre-existing library. Accordingly, the alternative will be referred to as the "active" method. As seen in FIG. 4 the step of establishing the reference transfer function includes substeps 102A, 104A, 108A analogous to steps 102, 104, 108 of FIG. 3. These substeps involve a referee sample $S_{REFEREE}$ and include 1) illuminating the referee sample with incident light radiation exhibiting P polarization types and having a known intensity (step 102A), 2) for each of the P polarization types inspecting the scattered light $R_X$ for the presence and intensity of each of Q polarization types (step 104A), and 3) establishing the relationship or transfer function $M_{REFEREE}$ (step 108A). The reference transfer function $M_{REF}$ delivered to comparison block 112 is $M_{REFEREE}$.

The active method may be useful when there is reason to believe that a particular condition of interest or concern is present in the sample S. In one variant the established referee transfer function $M_{REFEREE}$ corresponds to a tissue condition known or believed to be present in a referee tissue sample $S_{REFEREE}$. In that case a favorable comparison between the transfer functions of the sample S and the referee sample at block 112 suggests that the known or believed condition is present in the samples. An unfavorable comparison suggests that the known or believed condition is not present in the sample (although some other condition may be). In another variant the referee tissue sample may be one that is considered to be a healthy tissue sample, at least with respect to the condition of interest. In that case a favorable comparison at block 112 suggests that the condition of interest is not present in sample S (although some other condition may be). An unfavorable comparison suggests some difference between the sample S and the healthy referee sample, but may be otherwise inconclusive.

Figure 5:
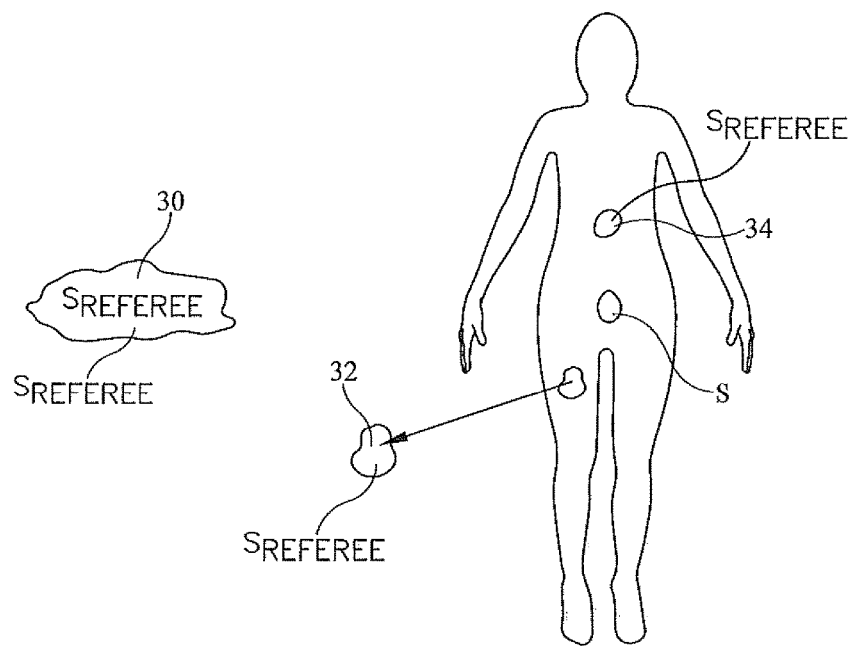
FIG. 5 is an illustration showing alternative sources for a referee tissue sample for use in the method of FIG. 4.

Referring to FIG. 5, irrespective of whether the referee sample is believed to exhibit a condition of interest or is considered to be healthy, the referee sample may be a previously acquired specimen 30 from the person under evaluation or from another person. Alternatively the referee sample may be a real-time sample from the person whose tissue is under evaluation. The real-time referee sample may be excised from the person (referee sample 32) or it may be an in-situ sample (referee sample 34) from another site on the person's body which may be an anatomically comparable site. An anatomically comparable site is a site different from the site of sample S but which, when healthy, is believed to exhibit the same or similar light scattering properties as healthy tissue at the sample site. Additionally or alternatively the comparable site may be one which, when distressed by an unhealthy condition, is believed to exhibit the same or similar light scattering properties as tissue at the sample site distressed by the same unhealthy condition. The referee sample may also be a historical, in-situ sample. A historical in-situ referee sample is a region of tissue whose transfer function M was established at an earlier time. When a historical sample is used the sample of interest S may be the same region of tissue as the historical sample. Alternatively the sample of interest S could be from another region of the person's body. In another alternative the referee sample is based on a different person and may be at an anatomical site corresponding to the the anatomical site of interest on the patient, or may be at a comparable anatomical site.

When the tissue sample S whose condition is sought and the referee sample $S_{REFEREE}$ are from the same person, the site of sample S can be referred to as the target site and the site of the referee sample can be referred to as a sister site. A sister site is one whose tissue is believed to be a reasonably accurate surrogate for healthy tissue at the target site. Table 1 below shows one or more sister sites for a number of target sites.

TABLE 1

| Target Site | Sister Site |
| --- | --- |
| Left or right heel | Opposite (right or left) heel |
| Sacrum | Gluteus, offset laterally from sacrum, or Sternum |
| Any site where the tissue condition is a condition of interest | Same site at an earlier time. |

The above described active method has been presented as an alternative to using a library of transfer functions. However a transfer function developed according to the active method may be used in cooperation with the transfer functions from the library. In one such mode of use the transfer function developed under the active method is used to conduct a validation check of the method based on the library of transfer functions, or vice versa. In another mode of use the transfer function developed under the active method is used as if it were just another member of the library.

Figure 6:
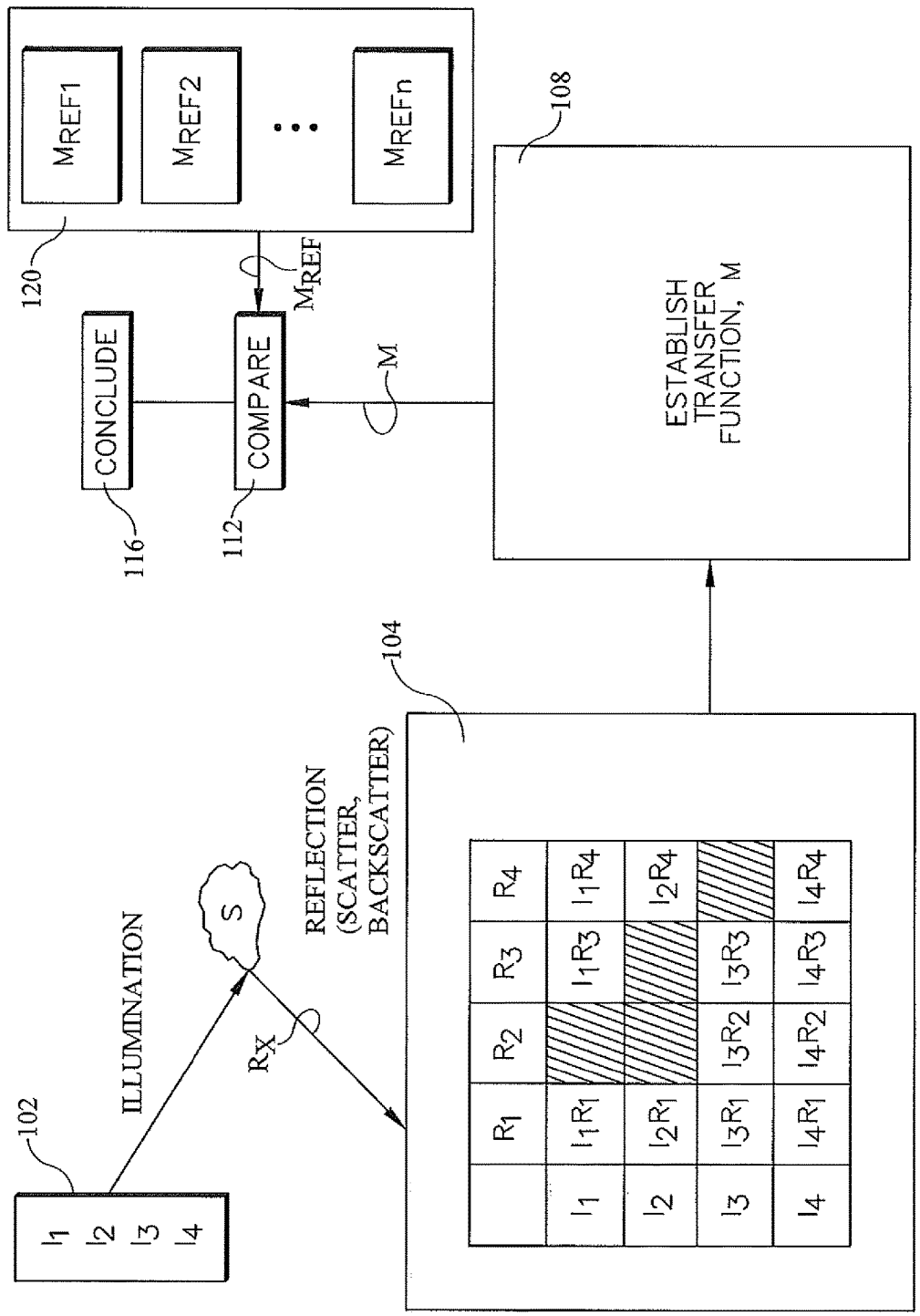
FIG. 6 is a flow chart similar to that of FIG. 3 but showing a method which carries out a partial inspection of light scattered from the tissue sample.

Referring back to FIG. 3, the method and variants thereof described so far are methods for which the chart of block 104 is fully populated. In other words the scatterings resulting from each and every one of the P incident types of polarized light are inspected for the presence and intensity of each and every one of the Q types of polarized light. FIG. 6 shows an example of an alternative method in which the scatterings from one or more of the P types of incident light (where P=4) are inspected for the presence and intensity of fewer than all of the Q types of polarized light (where Q=4). The crosshatched cells of the chart correspond to a given polarization type of incident radiation whose scattering $R_X$ has not been inspected for the Q type of polarized light indicated by the subscript of the column heading. Declining to inspect for one of the Q types of light is not the same as inspecting for that light and finding that the intensity is zero. Therefore the crosshatched cells of FIG. 6 are not analogues of cells in the fully populated chart in which the $I_j R_k$ value happens to be zero.

FIG. 6 shows the method of FIG. 3 modified so that the scattering from at least one of the P types of incident light is inspected for the presence and intensity of at least one but fewer than all of the Q-polarized types of light. The example of FIG. 6 is also a more specific case in which P=4 and Q=4. According to the method, sample S is illuminated with light which exhibits each of four different illumination types (block 102) and is of a known intensity. The light incident on the sample is designated by I and the type of polarization is designated by the subscripts 1, 2, 3, 4. For each of the four polarization types, the scattered light $R_X$ is inspected for the presence and intensity of at least one but not necessarily all of Q polarization types. Block 104 shows this in tabular format using the same notation as in FIG. 3. The light scattered from the sample as a result of the sample having been illuminated with type-1 polarized light of a known intensity is inspected for the presence and intensity of type-1, type-3 and type-4 polarized light, but not for type-2 polarized light. The light scattered from the sample as a result of the sample having been illuminated with type-2 polarized light is inspected for the presence and intensity of type-1 and type-4 polarized light, but not for type-2 and type-3 polarized light. The light scattered from the sample as a result of the sample having been illuminated with type-3 polarized light is inspected for the presence and intensity of type-1, type-2 and type-3 polarized light, but not for type-4 polarized light. The light scattered from the sample as a result of the sample having been illuminated with type-4 polarized light is inspected for the presence and intensity of type-1, type-2, type-3 and type-4 polarized light.

At block 108 the method establishes a relationship or transfer function M which relates the intensity and polarization type of the incident radiation to the intensity and polarization type of the scattered radiation. In particular block 108 relates the intensity of each of the P polarization types of the incident light to the intensity of the polarization type for which the scattered light was inspected.

After block 108 the method of FIG. 6 is the same as that of FIG. 3 including the variants and options already described in connection with FIG. 3

With the general outlines of the methods having now been established a number of variants and principles can be better appreciated.

In one variant P=4, Q=4, and the four P and Q polarization types are each selected from the three polarization groups of table 2 below. The first of the four polarization types is selected from a first one of the three polarization groups. The second of the four polarization types is selected from a second one of the three polarization groups. The third of the four polarization types is selected from a third one of the three polarization groups. The fourth polarization type is selected from any one of the three groups.

TABLE 2

| Polarization Group | Polarization Types |
| --- | --- |
| Single Component Linear | Linear horizontal polarization designated by H Linear vertical polarization designated by V |

TABLE 2-continued

| Polarization Group | Polarization Types |
|---|---|
| Dual Component Linear | +45° linear polarization designated by P$^+$, −45° linear polarization designated by P$^-$ |
| Circular | Right circular polarization designated by R, Left circular polarization designated by L |

When P and Q are equal to each other, each of the selected P polarization types can have an exact counterpart in the set of Q polarization types. For example if P=4 and Q=4 the set of P polarization types and the set of Q polarization types may both be H, V, and R (H, P$^+$, and R having each been selected from a different group of table 2 and V having been selected from any one of the groups, in this example the "single component linear" group).

In the methods described in this specification the incident and scattered light have been described as having a polarization type. Light can also be described as having a polarization state which is a function of the selected polarization types and light intensity.

The polarization state of light can be expressed in terms of the balances between the measurable intensities of H, V, P$^+$, P$^-$, R, and L polarized light and the total intensity of the light. This is conventionally written as a Stoke's vector:

$$\begin{bmatrix} I \\ Q \\ U \\ V \end{bmatrix} = \begin{bmatrix} \text{Total Intensity} \\ H-V \\ P^+ - P^- \\ R-L \end{bmatrix} \tag{1}$$

In one specific example the polarization state of the incident light is input Stoke's vector $[I, H-V, P^+-P^-, R-L]^T_{IN}$ and the polarization state of the output light is output Stoke's vector $[I, H-V, P^+-P^-, R-L]^T_{OUT}$ where the T signifies the transpose of the vector, and wherein the transfer function M is a 4×4 matrix referred to as a transport matrix or Mueller matrix. Each vector element is a value of light intensity. For example element $(P^+-P^-)_{IN}$ denotes the difference in the intensities of P$^+$ polarized and P$^-$ polarized light incident on the sample; element $(R-L)_{OUT}$ denotes the difference in the intensities of R polarized and L polarized light scattered from the sample. The transfer function M satisfies the equation below in which the X symbol signifies a matrix cross product.

$$\begin{bmatrix} I \\ Q \\ U \\ V \end{bmatrix}_{OUT} = \begin{bmatrix} M11 & M12 & M13 & M14 \\ M21 & M22 & M23 & M24 \\ M31 & M32 & M33 & M34 \\ M41 & M42 & M43 & M44 \end{bmatrix} \times \begin{bmatrix} I \\ Q \\ U \\ V \end{bmatrix}_{IN} \tag{2}$$

where I, Q, P$^+$, P$^-$ U, and V are as defined above in equation (1). In practice the sample is successively illuminated with each of the four types of polarized input light. The illumination with only I-polarized light (but not Q-polarized, U-polarized or V-polarized light) yields four equations, specifically:

$$(M11) \times (I_{IN}) = I_{OUT}, \tag{2.1}$$

$$(M21) \times (I_{IN}) = Q_{OUT}, \tag{2.2}$$

$$(M31) \times (I_{IN}) = U_{OUT}, \tag{2.3}$$

$$(M41) \times (I_{IN}) = V_{OUT}, \tag{2.4}$$

where the lower case "x" signifies ordinary multiplication. Illumination with only Q-polarized light (but not I-polarized, U-polarized or V-polarized light) yields four similar equations:

$$(M12) \times (Q_{IN}) = I_{OUT}, \tag{2.5}$$

$$(M22) \times (Q_{IN}) = Q_{OUT}, \tag{2.6}$$

$$(M32) \times (Q_{IN}) = U_{OUT}, \tag{2.7}$$

$$(M42) \times (Q_{IN}) = V_{OUT}, \tag{2.8}$$

Illumination with only U-polarized light (but not I-polarized, Q-polarized or V-polarized light) yields four more similar equations:

$$(M13) \times (U_{IN}) = I_{OUT}, \tag{2.9}$$

$$(M23) \times (U_{IN}) = Q_{OUT}, \tag{2.10}$$

$$(M33) \times (U_{IN}) = U_{OUT}, \tag{2.11}$$

$$(M43) \times (U_{IN}) = V_{OUT}, \tag{2.12}$$

Illumination with only V-polarized light (but not I-polarized, Q-polarized or U-polarized light) yields four more similar equations:

$$(M14) \times (V_{IN}) = I_{OUT}, \tag{2.13}$$

$$(M24) \times (V_{IN}) = Q_{OUT}, \tag{2.14}$$

$$(M34) \times (V_{IN}) = U_{OUT}, \tag{2.15}$$

$$(M44) \times (V_{IN}) = V_{OUT}, \tag{2.16}$$

The foregoing sixteen equations can be used to determine the sixteen unknowns (the $M_{ij}$ values).

When establishing the elements of the output vector it is necessary to inspect for and measure only four of the six polarized light intensities. This is because of the equivalences of equation (3):

$$H+V=P^++P^-=R+L \tag{3}$$

Figure 7:
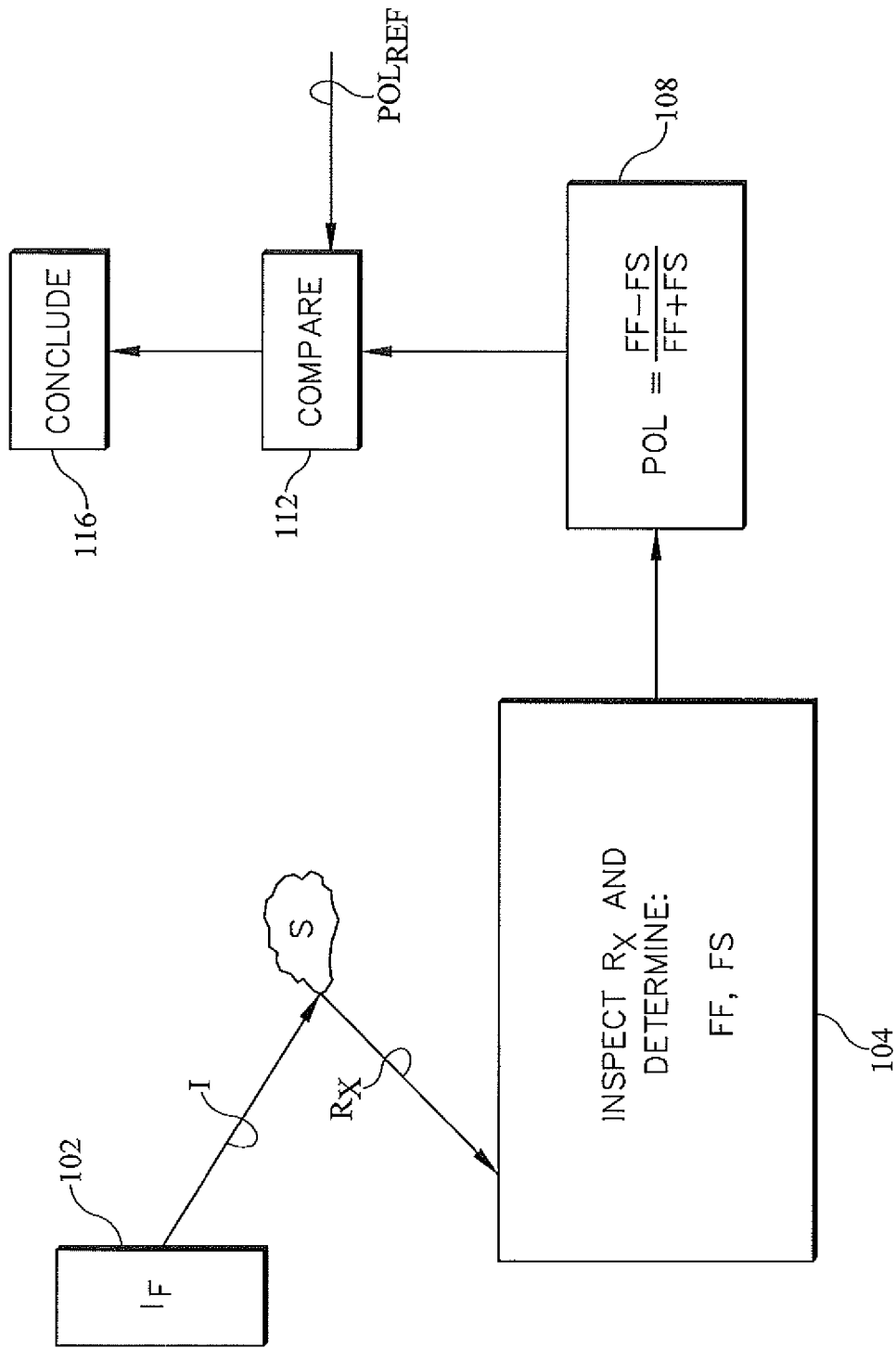
FIG. 7 is a flow chart illustrating a simplified method of assessing the condition of a tissue sample, in particular whether the tissue sample exhibits a pressure ulcer or a precursor to a pressure ulcer. The method uses only one type of incident polarized light to illuminate the sample and inspects the scattered light for only two types of polarization.

FIG. 7 shows a simplified variation of the method which assesses whether the tissue sample exhibits a pressure ulcer or a precursor to a pressure ulcer. In the simplified method only one type of polarization, a first type F is used to illuminate the sample. The scattered light is inspected for only two types of polarization, the first type F and a second type S. The method includes illuminating a tissue sample S with light polarized to exhibit the first type of polarization (block 102). At block 104 The method determines intensities FF (first/first) and FS (first/second). FF is the intensity of light which is scattered from the sample and which exhibits the first type of polarization F as a result of having been illuminated with light having the first type of polarization F. FS is the intensity of light which is scattered from the sample and which exhibits the second type of polarization S as a result of having been illuminated with light having the first type of polarization F.

At block 108 the method establishes a polarization ratio POL defined by $$POL = \frac{FF - FS}{FF + FS}. \quad (4)$$

At block 112 the method compares the established relationship, i.e. the established ratio POL, to one or more reference pressure ulcer relationships $POL_{REF}$. At block 116 the method reaches a conclusion, based on the comparison, about the likelihood that the polarization ratio reveals either a pressure ulcer or a precursor to a pressure ulcer.

As with the less simplified method and its variants, the polarization types are selected from:
 a) linear horizontal polarization designated by H,
 b) linear vertical polarization designated by V,
 c) +45° linear polarization designated by P⁺,
 d) −45° linear polarization designated by P⁻,
 e) right circular polarization designated by R, and
 f) left circular polarization designated by L.

Figure 8:
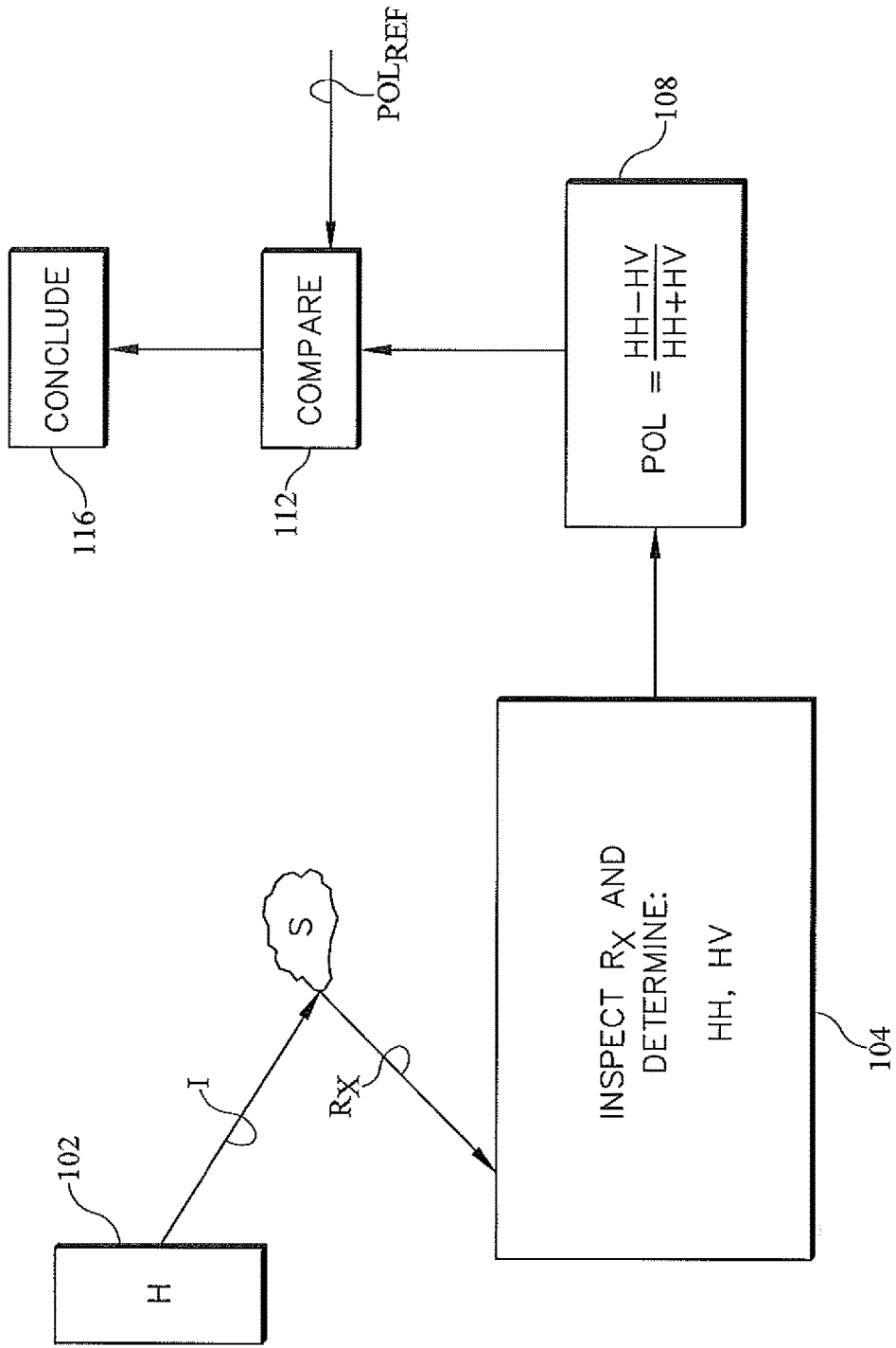
FIG. 8 is a flow chart similar to that of FIG. 7 showing one specific embodiment of the simplified method of FIG. 7 in which the incident light is H-polarized and the scattered light is inspected for H and V polarization.

FIG. 8 shows one specific embodiment of the simplified method in which the first and second types of polarization are H and V, and the polarization ratio is:

$$POL = \frac{HH - HV}{HH + HV} \quad (5)$$

Figure 9:
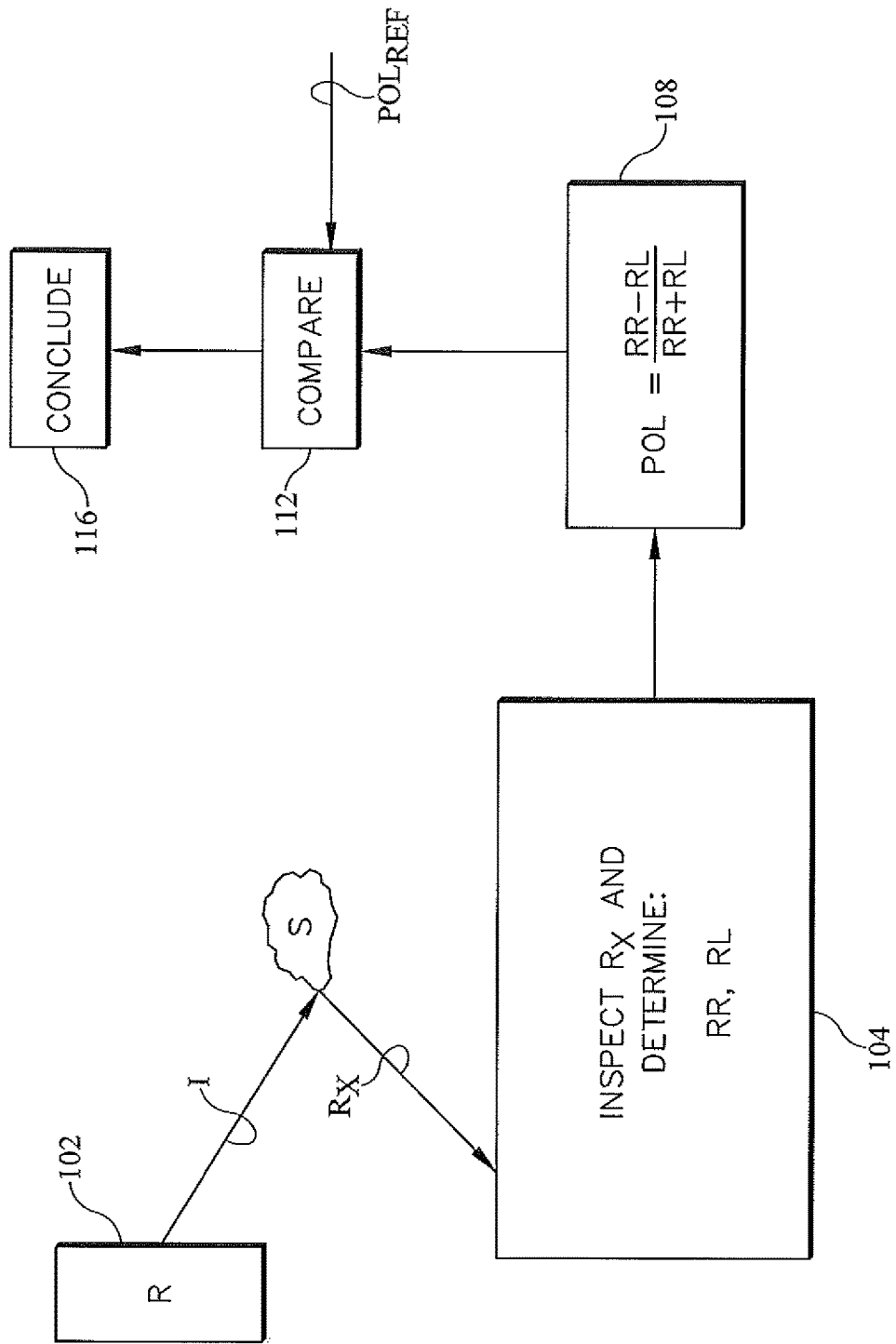
FIG. 9 is a flow chart similar to that of FIG. 7 showing another specific embodiment of the simplified method of FIG. 7 in which the incident light is R-polarized and the scattered light is inspected for R and L polarization.

FIG. 9 shows another specific embodiment of the simplified method the first and second types of polarization are R and L, and the polarization ratio is:

$$POL = \frac{RR - RL}{RR + RL} \quad (6)$$

Figure 10:
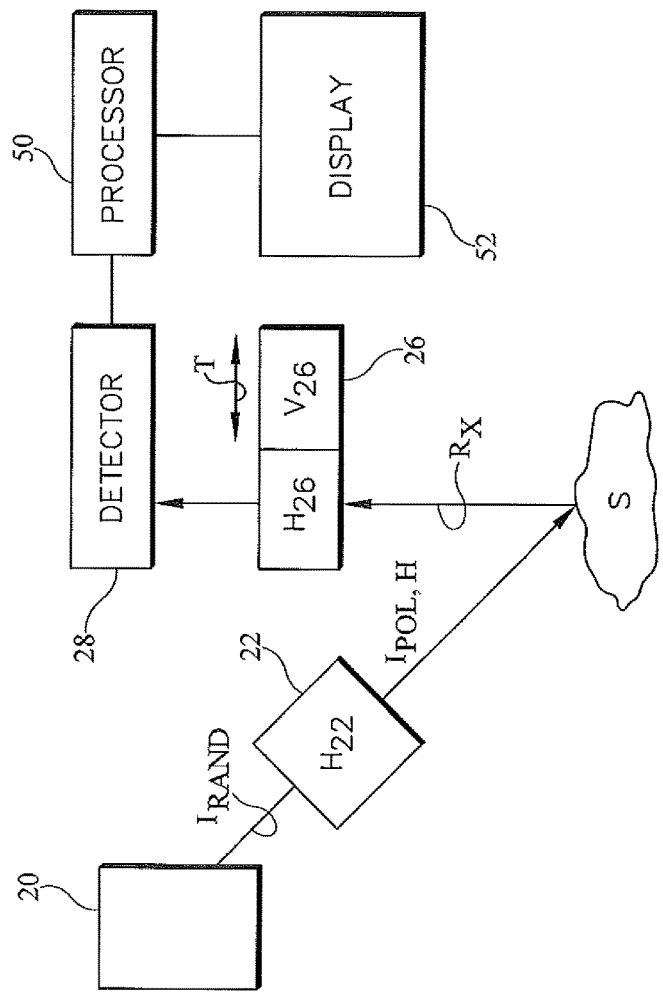
FIG. 10 is a schematic illustration showing an apparatus for carrying out the simplified method using aspects of the simplified method of FIG. 8 as an example.

FIG. 10 is a schematic illustration showing an apparatus for carrying out the simplified method. The illustrated apparatus includes a light source 20 which produces unpolarized or random light $I_{RAND}$ and a single polarizer 22. By way of example the polarizer polarizes the random light to exhibit linear horizontal polarization H as indicated by the label "$H_{22}$". The polarized light is labeled $I_{POL,H}$.

The apparatus also includes a polarizing filter array 26. In the example of FIG. 10 the polarizing filter array includes two members labeled $H_{26}$ and $V_{26}$. The polarizing filter array is translatable in direction T so that a user can align either filter $H_{26}$ or filter $V_{26}$ with light $R_X$ scattered from sample S. Only H-polarized light will pass through filter $H_{26}$ and therefore filter $H_{26}$ isolates H polarized scattered light. Only V polarized light will pass through filter $V_{26}$ and therefore filter $V_{26}$ isolates V polarized scattered light. Therefore the specific filters shown in FIG. 10 are suitable for carrying out methods based on HH and HV scattered light, as in FIG. 8. The illustrated apparatus also includes a detector 28, a processor 50 for processing information from the detector, and a display device 52 for displaying information.

Figure 11:
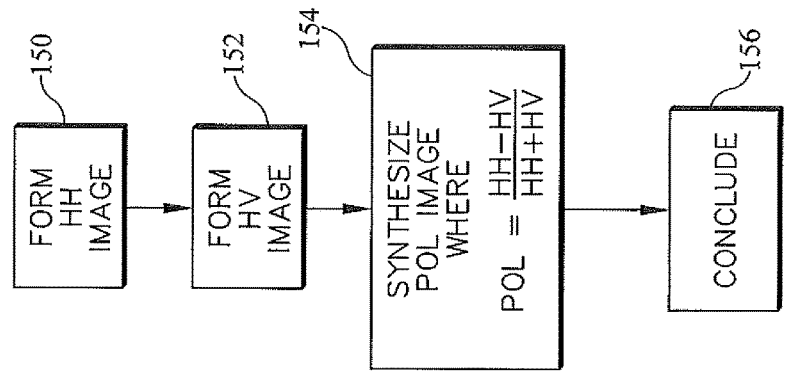
FIG. 11 is a block diagram of the method which uses the apparatus of FIG. 10.

FIG. 11 shows a block diagram of a method which uses the apparatus of FIG. 10. The method includes forming an HH image at block 150 and an HV image at block 152, although the order could be reversed. The HH image is based on H-polarized light scattered from sample S as a result of the sample having been illumiinated with H-polarized light. The HV image is based on V-polarized light scattered from sample S as a result of the sample having been illuminated with H-polarized light. The images can be a typical, human-comprehendable video images or can be an assemblages of information more adapted to machine interpretation (e.g. computer interpretation). Attributes of a human comprehendable image include that its information content can can be perceived by a human, typically with the sense of sight.

At block 154 the method uses the HH and HV images to construct a synthesized image designated $POL_{IMAGE}$ and which can be represented by equation (6) below:

$$POL_{IMAGE} = \frac{HH - HV}{HH + HV} \quad (7)$$

In the method as just described the formation of the HH and HV images need not be explicitly carried out provided the information required to construct the synthesized image is made available, for example by being retrievable from a computer memory or a charge coupled device in which the information had previously been stored.

The HH image is almost entirely the result of singly or doubly scattered photons which remain H-polarized after having been scattered (and which therefore are accurate indicators of tissue condition) as well as multiply scattered photons which are H-polarized (and which, because of the multiple scattering do not possess information about tissue condition). The HV image excludes the singly and doubly scattered H-polarized photons but, like the HH image, shows the contribution of multiply scattered H-polarized photons. The subtraction in the numerator (HH-HV) therefore subtracts a noise contribution (HV) from an image (HH) which includes both signal and noise. As a result the numerator represents only the signal contribution. The addition in the denominator preserves both signal and noise components. As a result the image formed at block 154 separates the signal (the numerator which shows the contributions of singly or doubly scattered photons which remain H-polarized after having been scattered and which are accurate indicators of tissue condition) from the combination of signal and noise represented by the denominator.

If the image synthesized at block 154 is a human comprehendable image a person can use that image at block 154 to conclude whether the image is consistent with a pressure ulcer or precursors to a pressure ulcer. If the image synthesized at block 154 is machine readable, the condition of the tissue sample can be interpreted by software executed by processor 50.

Although this disclosure refers to specific embodiments, it will be understood by those skilled in the art that various changes in form and detail may be made without departing from the subject matter set forth in the accompanying claims.

We claim:

1. A method for assessing the condition of a tissue sample comprising
 illuminating the sample with incident electromagnetic radiation exhibiting P polarization types;
 for each of the P polarization types, inspecting scattered incident radiation for at least one Q polarization type;
 establishing a transfer function M relating the intensity of the P polarization types of the incident radiation to the intensity of the polarization types for which of the scattered radiation was inspected;
 actively establishing one or more reference transfer functions, each established reference transfer function being associated with a referee tissue sample whose condition with respect to a condition of interest is known or believed, each of the established reference transfer functions being based on the intensity of one or more of the P polarization types of the incident radiation and the intensity of one or more of the Q polarization types of the scattered radiation;
comparing the established transfer function to one or more of the actively established reference transfer functions; and
reaching a conclusion about the condition of the tissue sample based on the comparison.

2. The method of claim 1 wherein the inspecting step for each of the P polarization types is carried out for all of the Q polarization types and wherein the transfer function has P X Q elements each of which corresponds to the intensity of one or more of the P polarization types and the intensity of one or more of the Q polarization types.

3. The method of claim 1 wherein:
P=4, Q=4 and the four P and Q polarization types are each selected from three polarization groups set forth below such that
the first polarization type is selected from a first polarization group,
the second polarization type is selected from a second polarization group,
the third polarization type is selected from a third polarization group, and
the fourth polarization type is selected from any one of the groups:

| Polarization Group | Polarization Types |
| --- | --- |
| Single Component Linear | Linear horizontal polarization designated by H |
|  | Linear vertical polarization designated by V |
| Dual Component Linear | +45° linear polarization designated by P+, |
|  | −45° linear polarization designated by P− |
| Circular | Right circular polarization designated by R, |
|  | Left circular polarization designated by L. |

4. The method of claim 3 wherein each of the four selected P polarization types is an exact counterpart of one of the four Q polarization types.

5. The method of claim 1 wherein:
P=4, Q=4 and the P and Q polarization types are:
a) linear horizontal polarization designated by H,
b) linear vertical polarization designated by V,
c) +45° linear polarization designated by P+, and
d) right circular polarization designated by R.

6. The method of claim 1 wherein the established transfer function relates an intensity and polarization type of the incident radiation to an intensity and polarization type of the scattered radiation.

7. The method of claim 1 wherein the conclusion is whether or not a pressure ulcer or a condition consistent with an incipient pressure ulcer is present in the sample.

8. The method of claim 1 wherein the polarization types of the incident radiation and the polarization types of the scattered radiation are selected from:
a) linear horizontal polarization designated by H,
b) linear vertical polarization designated by V,
c) +45° linear polarization designated by P+,
d) −45° linear polarization designated by P−,
e) right circular polarization designated by R, and
f) left circular polarization designated by L.

9. The method of claim 8 wherein the incident radiation has a polarization state, the scattered radiation has a polarization state, the polarization state of the incident radiation is defined in terms of:
A) total intensity I of unpolarized radiation which is used to carry out the illuminating step,
B) intensity of H minus intensity of V of the incident radiation,
C) intensity of P+ minus intensity of P− of the incident radiation, and
D) intensity of R minus intensity of L of the incident radiation; and
the polarization state of the scattered radiation is defined by:
A) total intensity I of unpolarized scattered radiation,
B) intensity of H minus intensity of V of the scattered radiation,
C) intensity of P+ minus intensity of P− of the scattered radiation, and
D) intensity of R minus intensity of L of the scattered radiation.

10. The method of claim 9 wherein the polarization state of the incident radiation is vector $[I, H-V, P^+-P^-, R-L]^T_{IN}$ and the polarization state of the output radiation is vector $[I, H-V, P^+-P^-, R-L]^T_{OUT}$ where the T signifies the transpose of the vector, and wherein the transfer function M is a 4×4 matrix.

11. The method of claim 10 wherein the transfer function M satisfies the matrix cross product:

$$\begin{bmatrix} I \\ Q \\ U \\ V \end{bmatrix}_{OUT} = \begin{bmatrix} M11 & M12 & M13 & M14 \\ M21 & M22 & M23 & M24 \\ M31 & M32 & M33 & M34 \\ M41 & M42 & M43 & M44 \end{bmatrix} \times \begin{bmatrix} I \\ Q \\ U \\ V \end{bmatrix}_{IN}$$

where: I is total light intensity, $Q=H-V$, $U=P^+-P^-$, and $V=R-L$.

12. The method of claim 1 wherein the step of illuminating the sample comprises sequentially illuminating the sample with each of the P polarization types.

13. The method of claim 1 wherein the incident electromagnetic radiation is selected from a portion of the electromagnetic spectrum which encompasses infrared, visible and ultraviolet wavelengths.

14. The method of claim 1 wherein the incident electromagnetic radiation has a wavelength selected to penetrate the tissue to a prescribed depth and to scatter more strongly from the tissue at the prescribed depth and to scatter less strongly from less deep tissue.

15. The method of claim 14 wherein the selected wavelength is a wavelength to which the less deep tissue is substantially transparent.

16. The method of claim 1 wherein the tissue sample whose condition is sought and the referee tissue sample or samples are in-situ samples.

17. The method of claim 16 wherein the in-situ referee tissue sample is from a site on the person's body which is anatomically comparable to the site of the sample whose condition sought.

18. The method of claim 16 wherein the in-situ referee tissue sample is a historical sample and is from the same region of tissue as the sample whose condition is sought.

19. The method of claim 16 wherein the tissue sample whose condition is sought is at a target site and the referee tissue sample is at one or more sister sites as set forth below:

| Target Site | Sister Site |
|---|---|
| Left or right heel | Opposite (right or left) heel |
| Sacrum | Gluteus, offset laterally from sacrum, or Sternum |
| Any site where the tissue condition is a condition of interest | Same site at an earlier time. |

20. The method of claim 1 wherein the referee sample is a historical sample from the same region of tissue as the sample whose condition is sought.

21. The method of claim 1 wherein the referee sample is a historical sample from another region of the person's body.

22. The method of claim 1 wherein the referee sample is based on a different person and the referee sample is at an anatomical site corresponding to the anatomical site of interest on the patient, or at a comparable anatomical site.

* * * * *